(12) United States Patent
Chang et al.

(10) Patent No.: US 9,855,446 B2
(45) Date of Patent: Jan. 2, 2018

(54) ROBOT

(71) Applicant: Daegu Gyeongbuk Institute of Science and Technology, Daegu (KR)

(72) Inventors: Pyung Hun Chang, Seoul (KR); Gezgin Erkin, Izmir (TR)

(73) Assignee: Daegu Gyeongbuk Institute of Science and Technology, Daegu (KR)

(*) Notice: Subject to any disclaimer, the term of this patent is extended or adjusted under 35 U.S.C. 154(b) by 309 days.

(21) Appl. No.: 14/541,077

(22) Filed: Nov. 13, 2014

(65) Prior Publication Data
US 2015/0283697 A1 Oct. 8, 2015

(30) Foreign Application Priority Data
Apr. 7, 2014 (KR) .................. 10-2014-0041388

(51) Int. Cl.
*A61N 5/10* (2006.01)
*A61B 6/00* (2006.01)
*B25J 9/00* (2006.01)
*B25J 18/00* (2006.01)
*A61N 5/01* (2006.01)

(52) U.S. Cl.
CPC .......... *A61N 5/1083* (2013.01); *A61B 6/4007* (2013.01); *A61B 6/44* (2013.01); *A61B 6/4458* (2013.01); *A61N 5/10* (2013.01); *A61N 5/1084* (2013.01); *B25J 9/0087* (2013.01); *B25J 18/007* (2013.01); *A61N 5/01* (2013.01); *Y10T 74/20305* (2015.01)

(58) Field of Classification Search
CPC ...... A61N 5/1083; A61N 5/1084; A61N 5/10; A61B 6/4007; A61B 6/44; A61B 6/4458
USPC .................. 378/9, 65, 68, 196, 197
See application file for complete search history.

(56) References Cited

U.S. PATENT DOCUMENTS

| 4,894,855 | A | * | 1/1990 | Kresse | .................. A61B 6/032 378/189 |
| 5,078,140 | A | * | 1/1992 | Kwoh | .................... A61B 34/30 378/20 |
| 5,549,439 | A | * | 8/1996 | Ploem | .................... A61B 6/102 378/204 |
| 5,635,721 | A | * | 6/1997 | Bardi | ....................... A61N 5/01 250/492.3 |

(Continued)

FOREIGN PATENT DOCUMENTS

| CN | 1942288 | 4/2007 |
| CN | 101304701 | 11/2008 |

(Continued)

OTHER PUBLICATIONS

Office Action for Chinese Patent Application No. 201480024010.7, dated Aug. 3, 2016.

(Continued)

*Primary Examiner* — Allen C. Ho
(74) *Attorney, Agent, or Firm* — Marshall, Gerstein & Borun LLP (57) ABSTRACT

A robot includes a central member, and a plurality of robot arms, each having one end connected to the central member to rotate on a longitudinal axis of the central member, and the robot arms are connected to different portions of the central member to rotate independently and incoherently with respect to each other.

13 Claims, 7 Drawing Sheets

(56) References Cited

U.S. PATENT DOCUMENTS

| | | | | |
|---|---|---|---|---|
| 6,200,024 B1* | 3/2001 | Negrelli | A61B 6/4233 | 378/196 |
| 6,213,638 B1* | 4/2001 | Rattner | A61B 6/4441 | 378/198 |
| 6,338,714 B1* | 1/2002 | Krause | A61G 12/004 | 128/897 |
| 6,435,715 B1* | 8/2002 | Betz | A61B 6/4458 | 378/197 |
| 6,530,688 B1* | 3/2003 | Müller | B25J 17/0266 | 378/197 |
| 6,582,121 B2* | 6/2003 | Crain | A61B 6/107 | 378/189 |
| 6,590,958 B2* | 7/2003 | Barber | A61B 6/107 | 378/196 |
| 6,592,259 B2* | 7/2003 | Crain | A61B 6/107 | 378/196 |
| 6,637,936 B2* | 10/2003 | Crain | A61B 6/107 | 378/162 |
| 6,644,852 B2* | 11/2003 | Crain | A61B 6/107 | 378/193 |
| 6,826,254 B2* | 11/2004 | Mihara | A61N 5/10 | 250/492.3 |
| 6,869,217 B2* | 3/2005 | Rasche | A61B 6/4441 | 378/193 |
| 6,977,987 B2* | 12/2005 | Yamashita | A61N 5/10 | 378/64 |
| 7,081,700 B2* | 7/2006 | Okumura | B25J 7/00 | 310/323.17 |
| 7,085,347 B2* | 8/2006 | Mihara | A61N 5/10 | 378/197 |
| 7,188,999 B2* | 3/2007 | Mihara | A61N 5/10 | 378/17 |
| 7,239,684 B2* | 7/2007 | Hara | A61N 5/1049 | 378/65 |
| 7,266,176 B2* | 9/2007 | Allison | A61N 5/1031 | 378/205 |
| 7,401,977 B2* | 7/2008 | Graumann | A61B 6/4441 | 378/197 |
| 7,441,953 B2* | 10/2008 | Banks | A61B 5/1038 | 378/197 |
| 7,500,784 B2* | 3/2009 | Grebner | A61B 6/4441 | 378/193 |
| 7,505,559 B2* | 3/2009 | Kuduvalli | A61N 5/1049 | 378/205 |
| 7,508,913 B2* | 3/2009 | Boese | A61B 6/12 | 378/205 |
| 7,530,739 B2* | 5/2009 | Lurz | A61B 6/4441 | 378/197 |
| 7,590,219 B2* | 9/2009 | Maurer, Jr. | A61N 5/103 | 378/145 |
| 7,594,751 B2* | 9/2009 | Grebner | A61B 6/4014 | 378/196 |
| 7,620,144 B2* | 11/2009 | Bodduluri | A61B 6/02 | 378/41 |
| 7,623,623 B2* | 11/2009 | Raanes | A61N 5/1049 | 378/205 |
| 7,693,257 B2* | 4/2010 | Allison | A61N 5/103 | 378/108 |
| 7,720,196 B2* | 5/2010 | Zhang | A61B 5/113 | 378/65 |
| 7,724,870 B2* | 5/2010 | Maltz | A61B 6/025 | 378/189 |
| 7,891,935 B2* | 2/2011 | Kremerman | B25J 9/042 | 414/744.5 |
| 7,894,649 B2* | 2/2011 | Fu | A61N 5/1049 | 378/65 |
| 7,905,658 B2* | 3/2011 | Groβ | | 378/193 |
| 7,934,869 B2* | 5/2011 | Ivanov | A61N 5/1049 | 378/20 |
| 7,938,579 B2* | 5/2011 | Groβ | A61B 6/4458 | 378/197 |
| 7,945,021 B2* | 5/2011 | Shapiro | A61B 6/032 | 378/19 |
| 7,972,061 B2* | 7/2011 | Groβ | A61B 6/4441 | 378/197 |
| 7,978,817 B2* | 7/2011 | Rietzel | A61N 5/1049 | 378/197 |
| 7,985,023 B2* | 7/2011 | Groβ | A61B 6/4441 | 378/194 |
| 7,988,357 B2* | 8/2011 | Hornung | A61B 6/4233 | 378/197 |
| 8,011,828 B2* | 9/2011 | Beimler | B25J 9/104 | 378/189 |
| 8,113,711 B2* | 2/2012 | Beimler | B25J 9/104 | 378/189 |
| 8,126,114 B2* | 2/2012 | Naylor | A61N 5/1049 | 378/65 |
| 8,130,907 B2* | 3/2012 | Maurer, Jr. | A61B 6/00 | 378/65 |
| 8,180,020 B2* | 5/2012 | Kilby | A61N 5/1031 | 378/65 |
| 8,262,554 B2* | 9/2012 | Sayeh | A61B 6/032 | 378/65 |
| 8,295,435 B2* | 10/2012 | Wang | A61N 5/10 | 378/65 |
| 8,303,575 B2* | 11/2012 | Rodriguez Y Baena | A61B 34/70 | 606/1 |
| 8,315,356 B2* | 11/2012 | Core | A61N 5/1049 | 378/205 |
| 8,320,517 B2* | 11/2012 | Dennerlein | A61B 6/032 | 378/4 |
| 8,459,867 B2* | 6/2013 | Muller | A61B 6/4464 | 378/196 |
| 8,483,358 B2* | 7/2013 | Allison | A61B 6/00 | 378/65 |
| 8,534,915 B2* | 9/2013 | Maschke | A61B 6/4411 | 378/196 |
| 8,559,596 B2* | 10/2013 | Thomson | G06T 7/0014 | 378/20 |
| 8,606,348 B2* | 12/2013 | Maschke | A61B 6/505 | 600/425 |
| 8,611,495 B2* | 12/2013 | Maschke | A61B 6/4014 | 378/197 |
| 8,824,630 B2* | 9/2014 | Maurer, Jr. | G06F 19/3481 | 378/20 |
| 8,849,633 B2* | 9/2014 | Core | G06F 19/3437 | 378/18 |
| 8,944,680 B2* | 2/2015 | Graumann | A61B 6/4452 | 250/491.1 |
| 8,989,846 B2* | 3/2015 | Kuduvalli | A61B 6/00 | 378/181 |
| 9,016,942 B2* | 4/2015 | Guo | A61B 6/4458 | 378/204 |
| 9,107,633 B2* | 8/2015 | Muller | A61B 6/0407 | |
| 9,108,048 B2* | 8/2015 | Maurer, Jr. | A61B 6/5247 | |
| 9,126,036 B2* | 9/2015 | Leek | A61N 5/1077 | |
| 9,149,656 B2* | 10/2015 | Tanabe | A61N 5/1067 | |
| 9,248,571 B2* | 2/2016 | Amberg | B25J 9/1664 | |
| 9,625,581 B2* | 4/2017 | Chang | B29C 67/0085 | |
| 2009/0041565 A1 | 2/2009 | Rodriguez Y Baena | | |
| 2012/0045308 A1 | 2/2012 | Kremerman | | |

FOREIGN PATENT DOCUMENTS

| | | |
|---|---|---|
| EP | 1 384 493 A1 | 1/2004 |
| JP | 2002-253687 A | 9/2002 |
| JP | 2004-283926 A | 10/2004 |
| KR | 20100119106 | 11/2010 |
| KR | 20-0451737 | 1/2011 |
| KR | 10-1334759 | 11/2013 |

OTHER PUBLICATIONS

Search Report for Chinese Patent Application No. 201480024010.7, dated Aug. 3, 2016.

(56) References Cited

OTHER PUBLICATIONS

Office Action for Japanese Patent Application No. 2016-512861, dated Jun. 21, 2016.
International Search Report for International application No. PCT/KR2014/010946 dated Dec. 23, 2014.
Office Action cited in KR 10-2014-0041388, dated Apr. 7, 2014.

* cited by examiner

ROBOT

CROSS-REFERENCE TO RELATED APPLICATION

This application claims the benefit of Korean Patent Application No. 10-2014-0041388, filed on Apr. 7, 2014, in the Korean Intellectual Property Office, the disclosure of which is incorporated herein by reference.

BACKGROUND

1. Field of the Invention

Embodiments of the present invention relate to a robot, and more particularly, to a robot that may aim at a target accurately and rapidly.

2. Description of the Related Art

Radiation therapy is a form of treatment to kill cancer cells using high-energy radiation. Radiation refers to a material mediating propagation or a phenomenon of energy propagating through a space, and an X-ray is a typical example of the radiation.

Radiation therapy is one of the three most prevalent cancer treatments, in company with surgery and chemotherapy. In general, radiation therapy may not require hospitalization, take a few to about 30 minutes per day, and be painless during treatment.

As radiation therapy apparatuses, X-Knife (Radionics, U.S.A.), Novalis Tx (BrainLAB, Germany), Peacok (NOMOS Corp., U.S.A.), Trilogy (Varian Medical System, U.S.A.), and CyberKnife (Accuray Inc., U.S.A.) are known. Many of the radiation therapy apparatuses are evolving to reduce an error occurring during treatment and increase an accuracy based on technology of Image Guided Radiotherapy (IGRT) and a linear accelerator.

CyberKnife is a high-precision stereotactic radiation therapy exclusive apparatus that may intensively irradiate a tumor portion in various directions by providing a small linear accelerator to a robot arm freely moving with six joints.

CyberKnife may provide a precise treatment by tracking coordinates of a gold marker inserted into a body and a skeleton image using real-time image guided technology, without an invasive fixing device. In addition, contrary to Gamma Knife used to treat brain tumors, CyberKnife may be used to treat cancer throughout a human body. Further, CyberKnite may be used for fractionated radiation therapy administered a few times, rather than once.

Recently, research is being conducted on CyberKnife. For example, Korean Patent Application No. 2009-0038051, filed on Apr. 30, 2009, discloses "System for radiotherapy planning information viewer".

SUMMARY

An aspect of the present invention provides a robot including a plurality of robot arms that may aim at a target more accurately and rapidly, thereby reducing a treatment or surgery time.

Another aspect of the present invention also provides a robot that may increase a directivity with respect to a target through easy control.

Still another aspect of the present invention also provides a robot that may be provided in a compact design to reduce an overall weight.

Yet another aspect of the present invention also provides a robot that may prevent a mutual collision between link members by rotating a plurality of link members independently and incoherently.

Further another aspect of the present invention also provides a robot including additional angle adjustment elements disposed at end portions of a second link member and a fourth link member or emitting members to efficiently adjust angles at which the emitting members face a target.

According to an aspect of the present invention, there is provided a robot including a central member, and a plurality of robot arms, each having one end connected to the central member to rotate on a longitudinal axis of the central member. The robot arms may be connected to different portions of the central member to rotate independently and incoherently with respect to each other.

The robot arms may include a plurality of link members, and a plurality of drive members to rotate the plurality of link members. The plurality of link members may be disposed on respective concentric spheres having an identical central point.

The plurality of link members may be provided in a form of arcs and disposed to be spaced from each other radially from the central point.

The plurality of link members may be disposed away from a location at which the plurality of link members is radially spaced from each other to incoherently rotate with respect to each other.

Extension lines of axes of the plurality of drive members may be positioned at an identical point.

The plurality of drive members may be disposed at end portions of the plurality of link members.

The axes of the drive members may be formed to be perpendicular to tangential directions of the end portions of the link members. Lengths of the link members may be determined based on angles between axes of the drive members.

Emitting members may be provided at other ends of the robot arms to be moved spherically along trajectories of rotation of the robot arms, respectively.

The emitting members may be disposed to be perpendicular to tangential directions of end portions of the robot arms, respectively.

Angle adjustment elements may be disposed at end portions of the robot arms or the emitting members to adjust angles at which the emitting members face a target, respectively.

According to another aspect of the present invention, there is also provided a robot including a central member, a first link member to rotate on a longitudinal axis of the central member, a first drive member disposed at one end of the first link member to transmit a torque to the first link member, a second link member connected to another end of the first link member to rotate on a first axis, and a second drive member disposed between the first link member and the second link member to transmit a torque to the second link.

The robot may further include a third link member connected to a portion of the central member, the portion differing from a portion to which the first link member is connected, to rotate on the longitudinal axis of the central member, a third drive member disposed at one end of the third link member to transmit a torque to the third link member, a fourth link member connected to another end of the third link member to rotate on a second axis, and a fourth drive member disposed between the third link member and the fourth link member to transmit a torque to the fourth link member.

The longitudinal axis of the central member, the first axis, and the second axis may be positioned at an identical location of a target.

The robot may further include emitting members disposed at end portions of the second link member and the fourth link member to face a target.

The first link member and the second link member may be disposed farther away from a target than the third link member and the fourth link member.

The fourth link member may be disposed closer to the target than the third link member.

When the third link member is disposed between the first link member and the second link member, a length of the third link member may be shorter than a length of the first link member, and the fourth link member may be disposed closer to the target than the second link member.

The robot may further include a fifth link member connected to a portion of the central member, the portion differing from portions to which the first link member and the third link member are connected, to rotate on the longitudinal axis of the central member, a fifth drive member disposed at one end of the fifth link member to transmit a torque to the fifth link member, a sixth link member connected to another end of the fifth link member to rotate on a third axis, a sixth drive member disposed between the fifth link member and the sixth link member to transmit a torque to the sixth link member, and an emitting member disposed at an end portion of the sixth link member to face a target. The longitudinal axis of the central member and the third axis may be positioned at an identical location of the target.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Reference will now be made in detail to exemplary embodiments of the present invention, examples of which are illustrated in the accompanying drawings, wherein like reference numerals refer to the like elements throughout.

Exemplary embodiments are described below to explain the present invention by referring to the figures.

Figure 1:
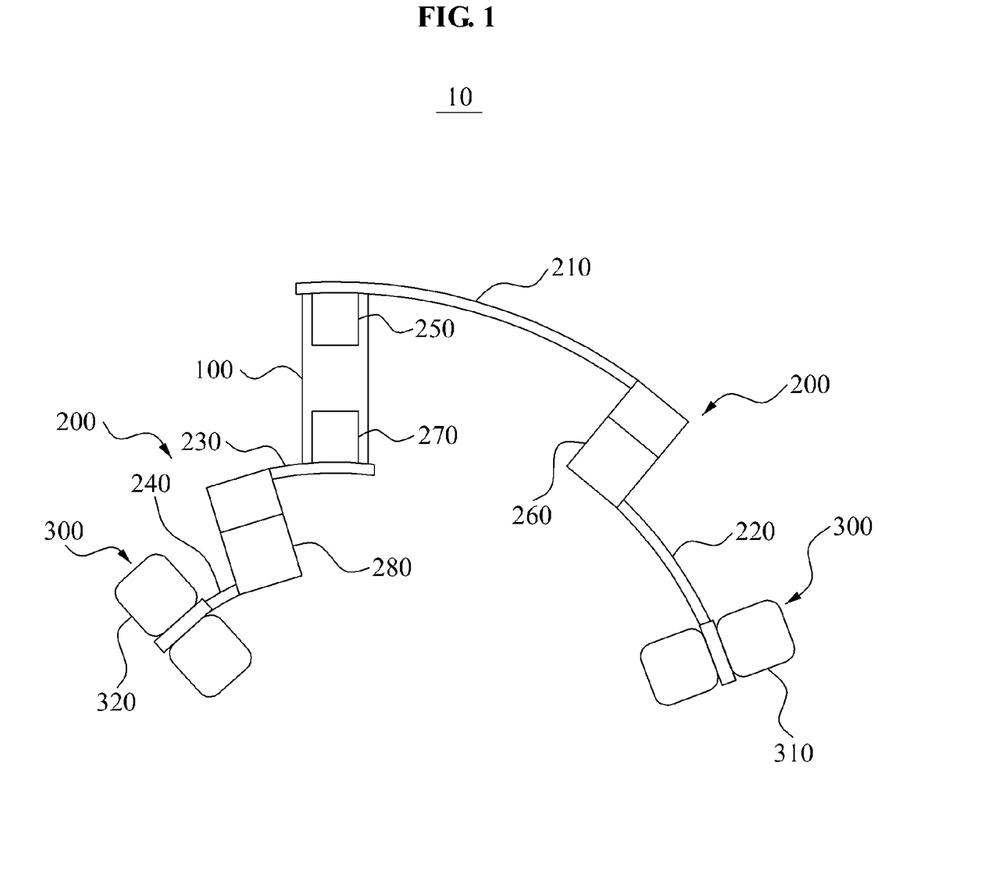
FIG. 1 is a view illustrating a robot according to an embodiment of the present invention.
Figure 2:
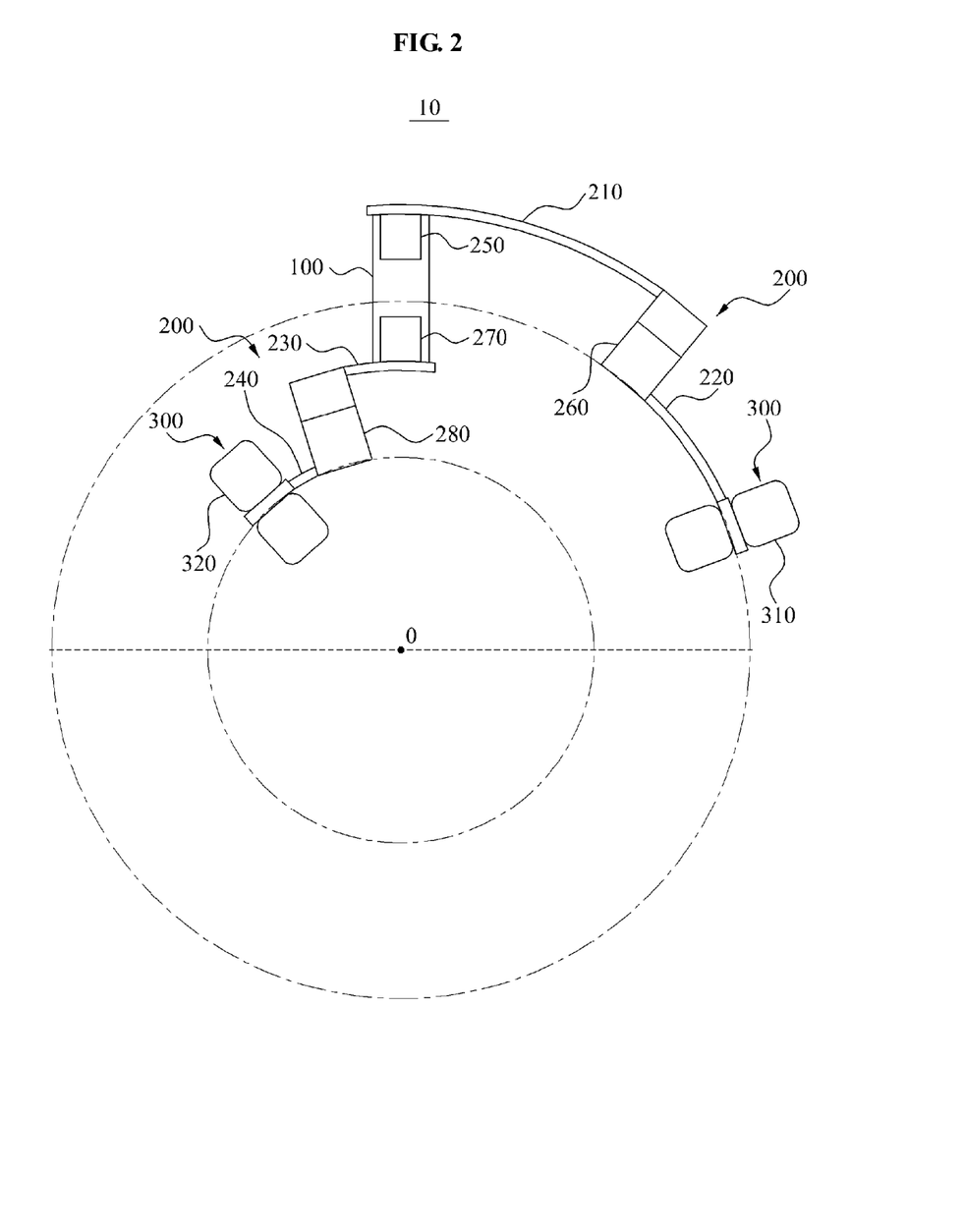
FIG. 2 is a view illustrating a disposition of link members in a robot according to an embodiment of the present invention.
Figure 3:
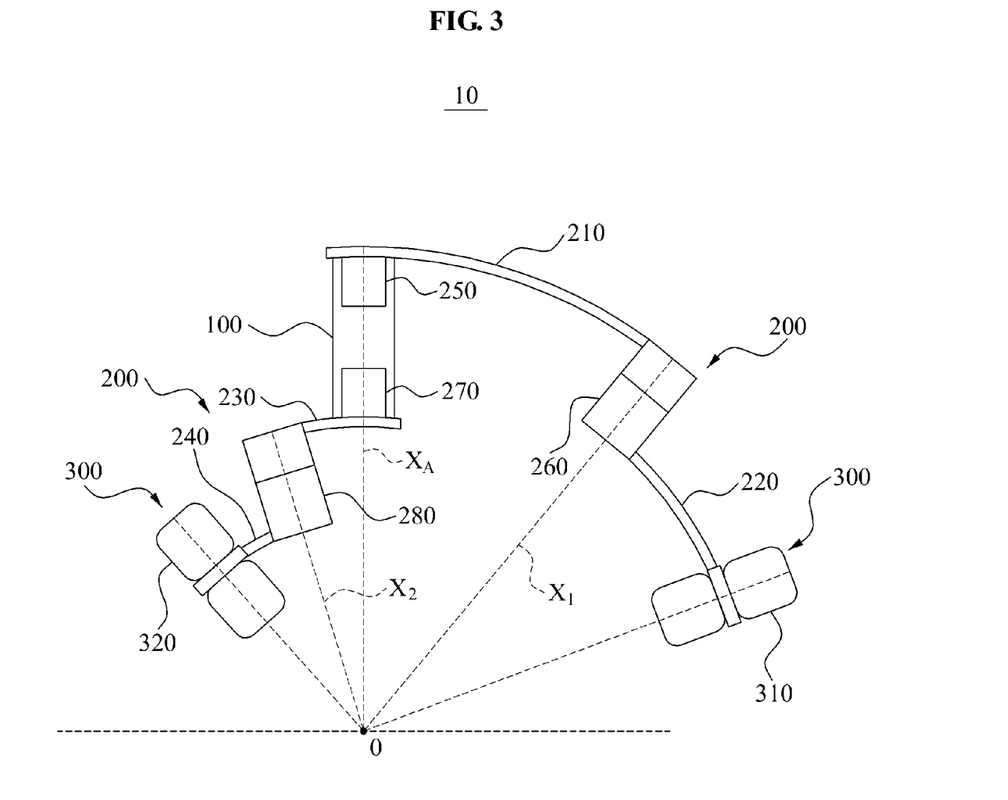
FIG. 3 is a view illustrating axes of drive members being positioned at an identical point in a robot according to an embodiment of the present invention.
Figure 4:
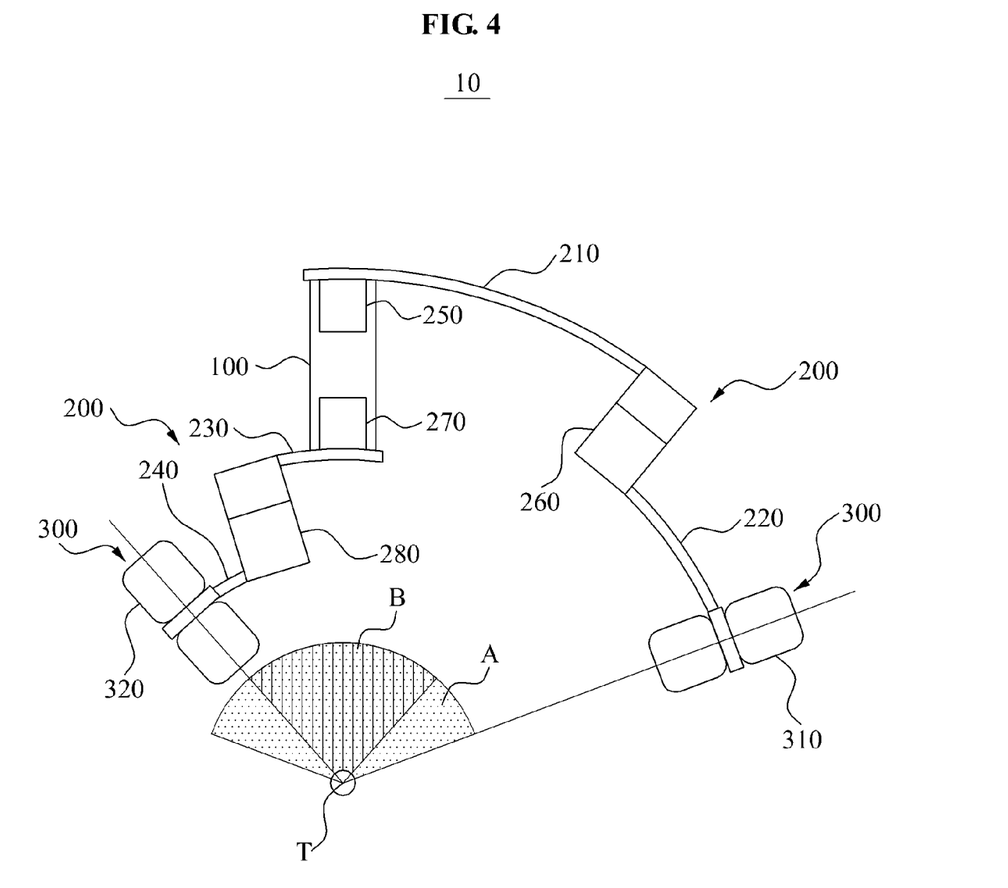
FIG. 4 is a view illustrating a radiation range of emitting members of a robot according to an embodiment of the present invention.
Figure 5:
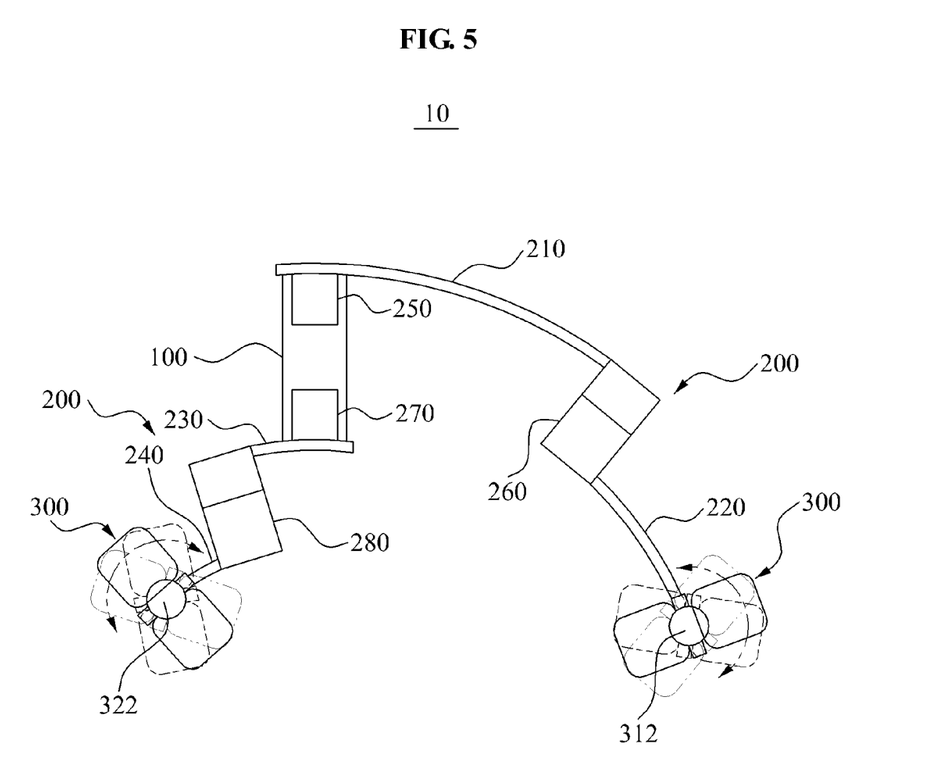
FIG. 5 is a view illustrating angle adjustment elements disposed in a robot according to an embodiment of the present invention.

FIG. 1 is a view illustrating a robot 10 according to an embodiment of the present invention. FIG. 2 is a view illustrating a disposition of link members 210 through 240 in the robot 10. FIG. 3 is a view illustrating axes of drive members 250 through 280 being positioned at an identical point in the robot 10. FIG. 4 is a view illustrating a radiation range of an emitting member 300 of the robot 10. FIG. 5 is a view illustrating angle adjustment elements disposed in the robot 10.

Referring to FIG. 1, the robot 10 may include a central member 100, and a plurality of robot arms 200 connected to both ends of the central member 100.

FIG. 1 illustrates two robot arms 200 provided in the robot 10. However, the present invention is not limited thereto. A number of robot arms 200 may vary.

The plurality of robot arms 200 may be connected to different portions of the central member 100. For example, the plurality of robot arms 200 may be disposed at an upper portion and a lower portion of the central member 10 to be spaced from each other. Thus, a length of the central member 100 may vary depending on a number of robot arms 200.

The central member 100 may have a longitudinal axis $X_A$. The plurality of robot arms 200 may rotate on the longitudinal axis $X_A$ of the central member 100. In this example, the plurality of robot arms 200 may be independently controlled to rotate in different directions or at different velocities. Further, the plurality of robot arms 200 may rotate independently and incoherently with respect to each other. Trajectories of rotation of the plurality of robot arms 200 may be present in different areas and thus, the plurality of robot arms 200 may rotate without a mutual collision.

Hereinafter, a structure of the robot arms 200 will be described with reference to FIGS. 2 and 3. When two robot arms 200 are provided in the robot 10, one robot arm 200 may be disposed at an upper portion of the central member 100, and the other robot arm 200 may be disposed at a lower portion of the central member 100.

The one robot arm 200 disposed at the upper portion of the central member 100 may include a first link member 210 and a second link member 220. The other robot arm 200 disposed at the lower portion of the central member 100 may include a third link member 230 and a fourth link member 240.

The first link member 210, the second link member 220, the third link member 230, and the fourth link member 240 may be disposed on concentric spheres, and disposed to be spaced from each other radially from a central point O.

The first link member 210, the second link member 220, the third link member 230, and the fourth link member 240 may be provided in a form of arcs, and have different lengths. However, the form of the first link member 210, the second link member 220, the third link member 230, and the fourth link member 240 is not limited thereto. The first link member 210, the second link member 220, the third link member 230, and the fourth link member 240 may be provided in an angular form.

The first link member 210 and the second link member 220 may be disposed on larger concentric spheres than the third link member 230 and the fourth link member 240. The first link member 210 may be disposed on a larger concentric sphere than the second link member 220. The third link member 230 may be disposed on a larger concentric sphere than the fourth link member 240.

When the first link member 210 and the second link member 220 are disposed on larger concentric spheres than the third link member 230 and the fourth link member 240 and located farther away from the central point O, a mutual collision may be prevented although the plurality of link members 210 through 240 simultaneously rotate. In addition, the first link member 210 and the second link member 220 may have greater lengths than the third link member 230 and the fourth link member 240. The first link member 210 may have a greater length than the second link member 220. The third link member 230 may have a greater length than the fourth link member 240.

As described above, the plurality of link members 210 through 240 may be disposed on concentric spheres to be spaced from each other and thus, rotate in different areas, thereby rotating incoherently. In this example, the plurality of link members 210 through 240 may rotate by means of a drive member.

A plurality of drive members may be provided. The plurality of drive members may include a first drive member 250, a second drive member 260, a third drive member 270, and a fourth drive member 280. The first drive member 250 may disposed at one end of the first link member 210 to transmit a torque to the first link member 210.

The first drive member 250 may be connected to be perpendicular to the one end of the first link member 210. The first drive member 250 may be connected to be perpendicular to a tangential direction at the one end of the first link member 210. For example, the first drive member 250 may be included in the central member 100. Although not illustrated in detail, it is obvious that the central member 100 may include a space in which the first drive member 250 is to be disposed.

The first drive member 250 may enable the first link member 210 to rotate on the longitudinal axis $X_A$ of the central member 100.

The first link member 210 may move along a trajectory of rotation on one of the concentric spheres by means of the first drive member 250.

The second drive member 260 may be disposed between the first link member 210 and the second link member 220 to transmit a torque to the second link member 220.

The second drive member 220 may rotate on a first axis $X_1$ extending from the central point O to the second drive member 260.

The first axis $X_1$ may be formed to tilt from the longitudinal axis $X_A$ of the central member 100. The longitudinal axis $X_A$ of the central member 100 and the first axis $X_1$ may extend to be positioned at an identical point, for example, the central point O.

The second drive member 260 may be connected to be perpendicular to one end of the second link member 220.

The second link member 220 may move along a trajectory of rotation on one of the concentric spheres by means of the second drive member 260. In this example, since the first link member 210 is disposed farther away from the central point O than the second link member 220, the trajectory of rotation of the first link member 210 may be greater than the trajectory of rotation of the second link member 220.

The third drive member 270 may be disposed at one end of the third link member 230 to transmit a torque to the third link member 230. Similar to the first drive member 250, the third drive member 270 may be included in the central member 100. Although not illustrated in detail, it is obvious that the central member 100 may include a space in which the third drive member 270 is to be disposed.

The third drive member 270 may also rotate on the longitudinal axis $X_A$ of the central member 100.

The first drive member 250 and the third drive member 270 may be provided separately or integrally.

When the first drive member 250 and the third drive member 270 are provided integrally, the first link member 210 and the third link member 230 may rotate in identical directions or at identical velocities.

Conversely, when the first drive member 250 and the third drive member 270 are provided separately, the first link member 210 and the third link member 230 may rotate independently. Since the third drive member 270 is disposed between the first link member 210 and the third link member 230, the third drive member 270 may be connected to be perpendicular to an end portion of the first link member 210 and an end portion of the third link member 230.

The third link member 230 may move along a trajectory of rotation on one of the concentric spheres by means of the third drive member 270 disposed as described above.

The trajectory of rotation of the third link member 230 may be smaller than the trajectories of rotation of the first link member 210 and the second link member 220. The trajectory of rotation of the third link member 230 may be closer to the central point O than the trajectories of rotation of the first link member 210 and the second link member 220.

The fourth drive member 280 may be disposed between the third link member 230 and the fourth link member 240 to transmit a torque to the fourth link member 240. The fourth link member 240 may rotate on a second axis $X_2$ extending from the central point O to the fourth drive member 280.

The second axis $X_2$ may be formed to tilt from the longitudinal axis $X_A$ of the central member 100. The longitudinal axis $X_A$ of the central member 100 and the second axis $X_2$ may be positioned at an identical point, for example, the central point O.

The fourth drive member 280 may be connected to be perpendicular to one end of the fourth link member 240. Since the third link member 230 and the fourth link member 240 may be disposed on concentric spheres, the fourth drive member 280 may be connected to be perpendicular to another end of the third link member 230.

The fourth link member 240 may move along a trajectory of rotation on one of the concentric spheres by means of the fourth drive member 280. In this example, since the fourth link member 240 is disposed closer to the central point O than the third link member 230, the trajectory of rotation of the fourth link member 240 may be smaller than the trajectory of rotation of the third link member 230.

Although not illustrated, the robot arms 200 may further include a fifth link member, a sixth link member, a fifth drive member, and a sixth drive member.

The fifth link member may be connected to a portion of the central member 100 to rotate on the longitudinal axis $X_A$ of the central member 100. The portion of the central member 100 to which the fifth link member is connected may differ from the portions to which the first link member 210 and the third link member 230 are connected.

The fifth link member may be disposed at an upper portion or a lower portion than the first link member 210 and the third link member 230.

The sixth link member may be disposed at another end of the fifth link member to rotate on a third axis. The third axis may be formed to tilt with respect to the longitudinal axis $X_A$ of the central member 100.

The fifth drive member may be disposed at one end of the fifth link member to transmit a torque to the fifth link member. Similar to the first drive member 250 and the third drive member 270, the fifth drive member may be included in the central member 100.

The sixth drive member may be disposed between the fifth link member and the sixth link member to transmit a torque to the sixth link member. In this example, the longitudinal axis $X_A$ of the central member 100 and the third axis may be positioned at the central point O or an identical location of a target.

A number of the drive members may be fewer than or equal to a number of the link members. As an example, a single drive member may be disposed at a single link member and thus, each link member may operate independently. As another example, a plurality of link members may be disposed at a single drive member and thus, the plurality of link members may operate simultaneously.

By way of the link members 210 through 240 and the drive members 250 through 280 configured as described above, the robot 10 may aim at a target or an affected area more accurately, and access to an area difficult to reach with a high degree of freedom.

In addition, the robot 10 may save a space occupied by the link members 210 through 240 and the drive members 250 through 280, and reduce an operation time through easy control over the link members 210 through 240 and the drive members 250 through 280.

The emitting member 300 may be disposed at another end of a robot arm 200.

Hereinafter, the emitting member 300 will be described based on a linear accelerator that emits radiation for radiation therapy. However, the emitting member 300 is not limited thereto. The emitting member 300 may emit another material including a liquid or gas. In detail, the emitting member 300 may include a first emitting member 310 disposed at an end portion of the second link member 220, and a second emitting member 320 disposed at an end portion of the fourth link member 240.

Similar to the second drive member 260 and the fourth drive member 280, the first emitting member 310 and the second emitting member 320 may be connected to be perpendicular to the end portion of the second link member 220 and the end portion of the fourth link member 240, respectively.

Accordingly, the first emitting member 310 and the second emitting member 320 may be provided to face the central point O, that is, the identical point at which the first axis $X_1$ of the second drive member 260 and the second axis $X_2$ of the fourth drive member 280 are positioned.

In addition, the first axis $X_1$ of the second drive member 260 and the second axis $X_2$ of the fourth drive member 280 may be positioned at the identical point, for example, the central point O, along with the longitudinal axis $X_A$ of the central member 100. Thus, the longitudinal axis $X_A$ of the central member 100, the first axis $X_1$, and the second axis $X_2$ may be positioned at the central point O, and the first emitting member 310 and the second emitting member 320 may also face the central point O.

When radiation is emitted from the emitting member 300 for treatment or surgery on a patient, the radiation may be emitted toward the central point O. In this example, since all of the axes of the drive members 250 through 280 face the central point O, the first emitting member 310 and the second emitting member 320 may be continuously aimed at the central point O while the link members 210 through 240 are rotating, due to a structural disposition of the link members 210 through 240 and the drive members 250 through 280.

Radiation may be emitted in a state in which a robot arm 200 is stationary. Thus, radiation may not be emitted while the robot arm 200 is moving to a subsequent emission point. However, when a plurality of robot arms 200 is provided, radiation may be emitted in a state in which remaining robot arms 200 are stationary while one robot arm 200 is moving. Thus, a treatment or surgery time may be reduced.

Referring to FIG. 4, a radiation area of the emitting member 300 is illustrated.

The first emitting member 310 may emit radiation within an area A through rotation of the first link member 210 and the second link member 220.

The second emitting member 320 may emit radiation within an area B through rotation of the third link member 230 and the fourth link member 240. In this example, since the first link member 210 and the second link member 220 are disposed farther away from the central point O than the third link member 230 and the fourth link member 240, the area A may be larger than the area B. In terms of three dimensions, the area A may represent a greater sphere than the area B.

The first emitting member 310 and the second emitting member 320 may emit radiation toward a target T within the area A and the area B at all times.

As described above, since the link members 210 through 240 may move spherically along trajectories of rotation, the first emitting member 310 disposed at the second link member 220 and the second emitting member 320 disposed at the fourth link member 240 may move spherically along the trajectories of rotation. Thus, the first emitting member 310 and the second emitting member 320 may be easily aimed at the target T.

Referring to FIG. 5, the angle adjustment elements may be additionally provided at end portions of the second link member 220 and the fourth link member 240 or the emitting member 300.

The angle adjustment elements may include a first angle adjustment element 312 disposed at a point at which the first emitting member 310 and the second link member 220 meet, and a second angle adjustment element 322 disposed at a point at which the second emitting member 320 and the fourth link member 240 meet.

The first emitting member 310 and the second emitting member 320 may oscillate while moving in directions of arrows on axes extending from the emitting member 300 toward the central point O.

The first emitting member 310 including the first angle adjustment element 312 and the second emitting member 320 including the second angle adjustment element 322 may perform small-angle movements. Thus, the first angle adjustment element 312 and the second angle adjustment element 322 may be useful when a minute angle adjustment is required after the first emitting member 310 and the second emitting member 320 aims at a target T by means of the drive members 250 through 280.

As described above, a robot according to an embodiment of the present invention may reduce a treatment or surgery time by aiming at a target more rapidly and accurately using a plurality of robot arms, increase a directivity with respect to the target through easy control, and reduce an overall weight through a compact design. In addition, the robot may prevent a mutual collision between a plurality of link members by rotating the link members independently and incoherently, and efficiently adjust an angle at which an emitting member faces the target through an additional angle adjustment element disposed at the emitting member.

Hereinafter, a kinematical analysis on a structure of the robot 10 will be described in detail. The following may be expressed based on forward kinematics.

$$x = f(\theta) \quad \text{[Equation 1]}$$

In the Equation 1, θ denotes a joint angle, and x denotes a location and direction of an end-effector. Coordinates of an emitting member may be estimated based on an angle at which link members are connected to each other.

In addition, when a Denavit-Hartenberg (D-H) convention is used, the kinematics of the robot may include four parameters, for example, a link length a of a line member, a link offset d, a link distortion α, and a joint angle θ. In this example, when a joint rotates around a z axis, transformation matrices may be expressed as follows.

$$\,^0_1T = \begin{bmatrix} c\theta1 & -c\alpha1s\theta1 & s\alpha1s\theta1 & 0 \\ s\theta1 & c\alpha1c\theta1 & -s\alpha1c\theta1 & 0 \\ 0 & s\alpha1 & c\alpha1 & R \\ 0 & 0 & 0 & 1 \end{bmatrix} \quad \text{[Transformation Matrix 1]}$$

$$\,^1_2T = \begin{bmatrix} c\theta2 & -c\alpha2s\theta2 & s\alpha2s\theta2 & 0 \\ s\theta2 & c\alpha2c\theta2 & -s\alpha2c\theta2 & 0 \\ 0 & s\alpha2 & c\alpha2 & 0 \\ 0 & 0 & 0 & 1 \end{bmatrix} \quad \text{[Transformation Matrix 2]}$$

In Transformation Matrices 1 and 2, s denotes sine, and c denotes cosine.

Through the above transformation matrices, a transformation matrix may be derived as follows.

$$\,^0_2T = \begin{bmatrix} c\theta1c\theta2 - c\alpha1s\theta1s\theta2 & s\alpha1s\alpha2s\theta1 - c\alpha2(c\alpha1c\theta2s\theta1 + c\theta1s\theta2) & c\alpha2s\alpha1s\theta1 + s\alpha2(c\alpha1c\theta2s\theta1 + c\theta1s\theta2) & 0 \\ c\theta2s\theta1 + c\alpha1c\theta1s\theta2 & -c\theta1s\alpha1s\alpha2 + c\alpha2(c\alpha1c\theta1c\theta2 - s\theta1s\theta2) & -c\theta1(c\alpha2s\alpha1 + c\alpha1c\theta2s\alpha2) + s\alpha2s\theta1s\theta2 & 0 \\ s\alpha1s\theta2 & c\alpha2c\theta2s\alpha1 + c\alpha1s\alpha2 & c\alpha1c\alpha2 - c\theta2s\alpha1s\alpha2 & R \\ 0 & 0 & 0 & 1 \end{bmatrix} \quad \text{[Transformation Matrix 3]}$$

The above transformation matrix may represent a case in which two link members are provided. A point to which relocation is to be performed by a translation, an offset, a scale, or a rotation on a three-dimensional (3D) coordinate system may be estimated using the transformation matrix.

In addition, a location and direction of the emitting member or the end-effector may be expressed as follows.

$$\,^0_2T = \begin{bmatrix} \,^0x_2 & \,^0y_2 & \,^0z_2 & \,^0p_2 \\ 0 & 0 & 0 & 1 \end{bmatrix} \quad \text{[Transformation Matrix 4]}$$

$$\,^0p_2 = \begin{bmatrix} 0 \\ 0 \\ R \end{bmatrix} \quad \text{[Transformation Matrix 5]}$$

In this example, the location of the emitting member or the end-effector may be constantly uniform.

Figure 6:
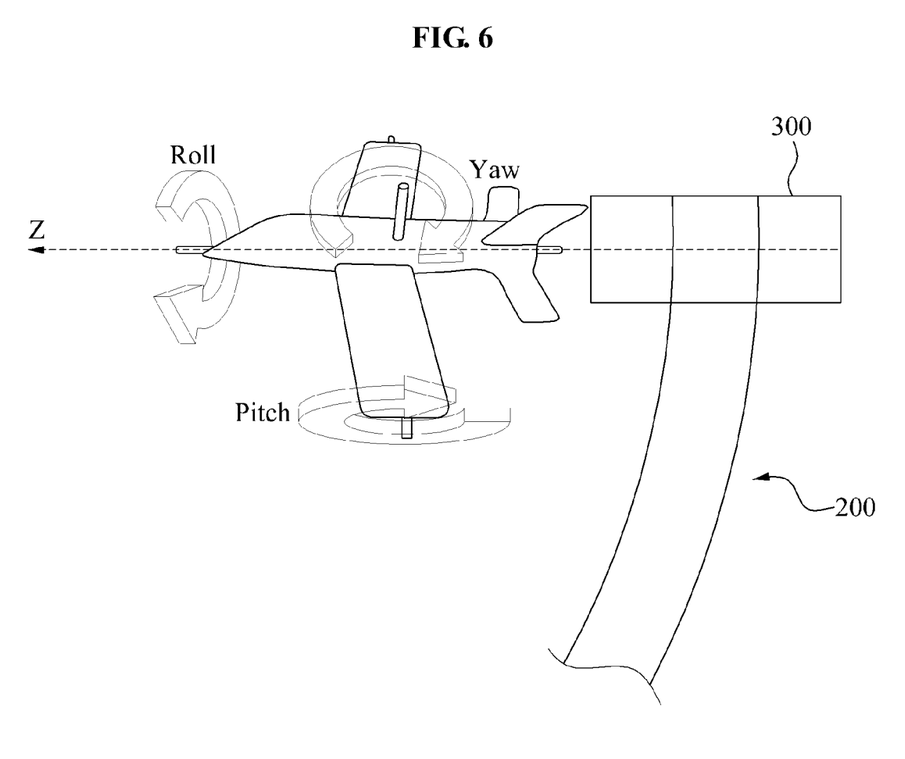
FIG. 6 illustrates a direction of an emitting member in a robot according to an embodiment of the present invention.

FIG. 6 illustrates a direction of an emitting member in a robot according to an embodiment of the present invention.

Referring to FIG. 6, the emitting member may face a z axis, and have a roll movement of rotating on the z axis, a yaw movement of oscillating up and down based on the z axis, and a pitch movement of rotating up and down based on the z axis. In this example, a roll direction may be insignificant in the emitting member. Only a z-vector may be considered for a direction of the emitting member. Thus, Transformation Matrix 2 may be arranged as follows.

$$\,^0z_2 = \begin{bmatrix} z_1 \\ z_2 \\ z_3 \end{bmatrix} = \begin{bmatrix} c\alpha2s\alpha1s\theta1 + s\alpha2(c\alpha1c\theta2s\theta1 + c\theta1s\theta2) \\ -c\theta1(c\alpha2s\alpha1 + c\alpha1c\theta2s\alpha2) + s\alpha2s\theta1s\theta2 \\ c\alpha1c\alpha2 - c\theta2s\alpha1s\alpha2 \end{bmatrix} \quad \text{[Transformation Matrix 6]}$$

Figure 7:
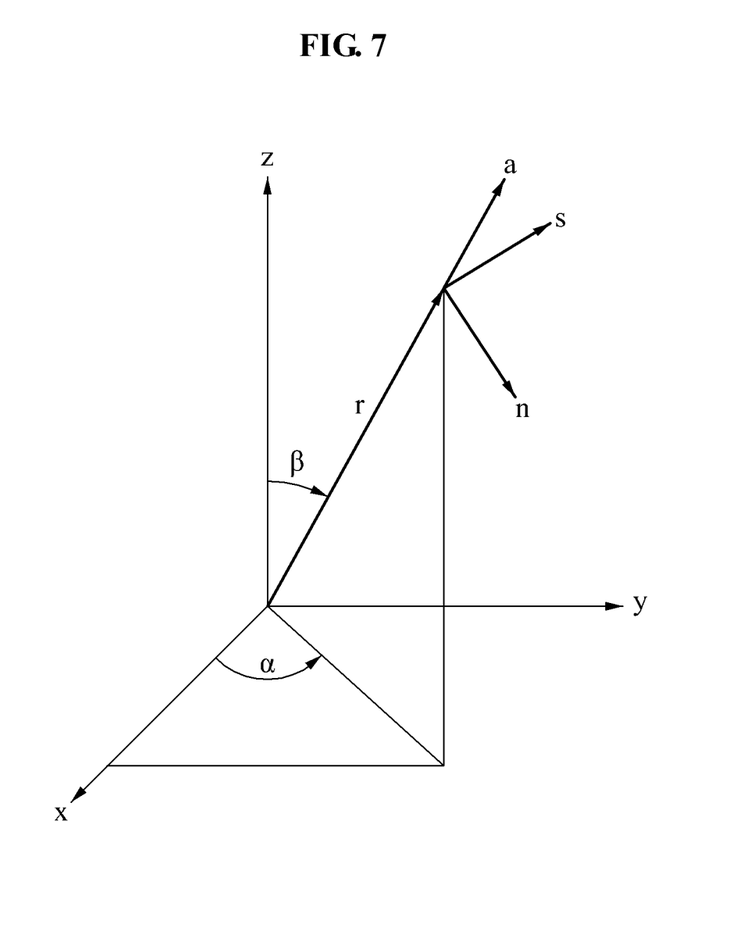
FIG. 7 illustrates spherical coordinates.

A desired direction of the emitting member may be designated as spherical coordinates α and β of FIG. 7. When the direction of the emitting member is given as α and β of FIG. 7, rotation matrices corresponding to the direction may be expressed as follows.

$$R_{spherical} = R_{z,\alpha}R_{y,\beta} = \begin{bmatrix} c\alpha c\beta & -s\alpha & c\alpha s\beta \\ s\alpha c\beta & c\alpha & s\alpha s\beta \\ -s\beta & 0 & c\beta \end{bmatrix} \quad \text{[Rotation Matrix 1]}$$

$$R_{spherical} = \begin{bmatrix} x_1 & y_1 & z_1 \\ x_2 & y_2 & z_2 \\ x_3 & y_3 & z_3 \end{bmatrix} \quad \text{[Rotation Matrix 2]}$$

Based on α and β from Rotation Matrices 1 and 2, $^0x_2=[x_1, x_2, X_3]^T$, $^0y_2=[y_1, y_2, y_3]^T$, and $^0z_2=[z_1, z_2, z_3]^T$ may be determined, and $\theta_1$ and $\theta_2$ may also be determined. Such a relationship may be expressed by inverse kinematics as follows.

$$\theta = f(x)^{-1} \quad \text{[Equation 2]}$$

In Equation 2, x denotes a vector $^0z_2=[z_1, z_2, z_3]^T$ and, θ denotes a vector including $\theta_1$ and $\theta_2$. Equation 2 may be an inverse function of Equation 1.

The joints angles $\theta_1$ and $\theta_2$ may be calculated based on orthonormal vectors $^0x_2$, $^0y_2$, and $^0z_2$. An intuitive method of calculating such vectors may be performed using spherical coordinates. When a direction is given as α and β, a rotation matrix corresponding to the direction may be expressed as follows.

$$R_{spherical} = R_{z,\alpha}R_{y,\beta} = \begin{bmatrix} c\alpha c\beta & -s\alpha & c\alpha s\beta \\ s\alpha c\beta & c\alpha & s\alpha s\beta \\ -s\beta & 0 & c\beta \end{bmatrix} \quad \text{[Rotation Matrix 3]}$$

In this example, constituent elements of the vectors may correspond to $^0x_2=[x_1, x_2, x_3]T$, $^0y_2 [y_1, y_2, y_3]$ and $^0z_2=[z_1, z_2, z_3]^T$.

The following Equations may be extracted from Transformation Matrix 3.

$$x_3 = s\alpha_1 s\theta_2$$

$$z_3 = c\alpha_1 c\alpha_2 - c\theta_2 s\alpha_1 s\alpha_2 \quad \text{[Equation 3]}$$

In Equation 3, $\theta_2$ may be induced as follows.

$$s\theta_2 = x_3 - s\alpha_1$$
$$c\theta_2 = \frac{z_3 + c\alpha_1 c\alpha_2}{s\alpha_1 s\alpha_2}$$
$$\tan\theta_2 = \frac{s\alpha_1 s\alpha_2 (x_3 - s\alpha_1)}{z_3 + c\alpha_1 c\alpha_2}$$
$$\theta_2 = \arctan2\left(x_3 - s\alpha_1, \frac{z_3 + c\alpha_1 c\alpha_2}{s\alpha_1 s\alpha_2}\right)$$

[Equation 4]

A function arctan 2, an arctangent function including two input variables, may be used due to a stability of being close to zero input values and a characteristic of a final angle returning to an appropriate quadrant.

$\theta_1$ may be calculated as follows. The following Equations 5 through 7 may be obtained from Transformation Matrix 4.

$$(x_2 = c\theta_2 s\theta_1 + c\alpha_1 c\theta_1 s\theta_2)c\alpha_1 s\theta_2$$
$$(x_1 = -s\theta_1 c\alpha_1 s\theta_2 + c\theta_1 c\theta_2)c\theta_2$$

[Equation 5]

$$c\alpha_1 s\theta_2 x_2 + c\theta_2 x_1 = c^2\alpha_1 s^2\theta_2 c\theta_1 + c^2\theta_2 c\theta_1$$
$$c\theta_1 = \frac{c\alpha_1 s\theta_2 x_2 + c\theta_2 x_1}{c_1^2 s^2\theta_2 + c^2\theta_2}$$

[Equation 6]

$$z_1 = (c\alpha_2 s\alpha_1 + s\alpha_2 c\alpha_1 c\theta_2)s\theta_1 + s\alpha_2 s\theta_2 c\theta_1$$
$$z_2 = -(c\alpha_2 s\alpha_1 + s\alpha_2 c\alpha_1 c\theta_2)c\theta_1 + s\alpha_2 s\theta_2 s\theta_1$$

[Equation 7]

In addition, the following may be assumed.

$$a = c\alpha_2 s\alpha_1 + s\alpha_2 c\alpha_1$$

$$b = s\alpha_2 s\theta_2$$

[Equation 8]

Through Equations 7 and 8, the following may be calculated.

$$a(z_1 = as\theta_1 + bc\theta_1)$$
$$b(z_2 = -ac\theta_1 + bs\theta_1)$$
$$az_1 = a^2 s\theta_1 + abc\theta_1$$
$$bz_2 = b^2 s\theta_1 - abc\theta_1$$
$$az_1 + bz_2 = (a^2 + b^2)s\theta_1$$
$$s\theta_1 = \frac{az_2 + bz_2}{a^2 + b^2}$$

[Equation 9]

Through Equations 6 and 9, $\theta_1$ may be calculated as follows.

$$\theta_1 = \arctan2\left(\frac{az_1 + bz_2}{a^2 + b^2}, \frac{c\alpha_1 s\theta_2 x_2 + c\theta_2 x_1}{c^2\alpha_1 s^2\theta_2 + c^2\theta_2}\right)$$

[Equation 10]

From Equations 4 and 10, the two joint angles $\theta_1$ and $\theta_2$ may be determined.

A Jacobian matrix will be described hereinafter. A linear mapping between a $\theta$-space and an x-space may be as follows. Equation 1 may be differentiated as follows.

$$^0\dot{x} = {^0}J\dot{\theta}$$

[Jacobian Matrix 1]

$$^0J = \begin{bmatrix} ^0z_0 \times (^0p_n - {^0}p_0) & ^0z_1 \times (^0p_n - {^0}p_1) \\ ^0z_0 & ^0z_1 \end{bmatrix}$$

The Transformation Matrix 1 may be expressed as follows.

$$^0_1T = \begin{bmatrix} ^0x_1 & ^0y_1 & ^0z_1 & ^0p_1 \\ 0 & 0 & 0 & 1 \end{bmatrix} =$$

[Rotation Matrix 7]

| $c\theta 1$ | $-c\alpha 1 s\theta 1$ | $s\alpha 1 s\theta 1$ | 0 |
|---|---|---|---|
| $s\theta 1$ | $c\alpha 1 c\theta 1$ | $-s\alpha 1 c\theta 1$ | 0 |
| 0 | $s\alpha 1$ | $c\alpha 1$ | R |
| 0 | 0 | 0 | 1 |

Thus, the Jacobian matrix may be expressed as follows.

[Jacobian Matrix 2]

$$^0J = \begin{bmatrix} \begin{bmatrix} 0 \\ 0 \\ 1 \end{bmatrix} \times \left(\begin{bmatrix} 0 \\ 0 \\ R \end{bmatrix} - \begin{bmatrix} 0 \\ 0 \\ 0 \end{bmatrix}\right) & \begin{bmatrix} s\alpha 1 s\theta 1 \\ -s\alpha 1 c\theta 1 \\ c\alpha 1 \end{bmatrix} \times \left(\begin{bmatrix} 0 \\ 0 \\ R \end{bmatrix} - \begin{bmatrix} 0 \\ 0 \\ R \end{bmatrix}\right) \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

[Jacobian Matrix 3]

$$^0J = \begin{bmatrix} ^0z_0 \times (^0p_n - {^0}p_0) & ^0z_1 \times (^0p_n - {^0}p_1) \\ ^0z_0 & ^0z_1 \end{bmatrix}$$

$$= \begin{bmatrix} \begin{bmatrix} 0 \\ 0 \\ 1 \end{bmatrix} \times \left(\begin{bmatrix} 0 \\ 0 \\ R \end{bmatrix} - \begin{bmatrix} 0 \\ 0 \\ 0 \end{bmatrix}\right) & \begin{bmatrix} s\alpha 1 s\theta 1 \\ -s\alpha 1 c\theta 1 \\ c\alpha 1 \end{bmatrix} \times \left(\begin{bmatrix} 0 \\ 0 \\ R \end{bmatrix} - \begin{bmatrix} 0 \\ 0 \\ R \end{bmatrix}\right) \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

$$= \begin{bmatrix} \begin{bmatrix} 0 \\ 0 \\ 0 \end{bmatrix} & \begin{bmatrix} 0 \\ 0 \\ 0 \end{bmatrix} \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

Thus, the Jacobian matrix may be expressed as follows.

$$J = \begin{bmatrix} 0 & s\alpha 1 s\theta 1 \\ 0 & -s\alpha 1 c\theta 1 \\ 1 & c\alpha 1 \end{bmatrix}$$

[Jacobian Matrix 4]

Through Jacobian Matrix 4, when only an angular velocity is considered and a translational velocity is not considered, a singularity may not be achieved except for a case in which $\alpha = n\pi$ and $n \in N$ are satisfied.

As described above, a relationship between a movement of a link member and a movement of an emitting member may be expressed through a Jacobian matrix. Thus, the movement of the emitting member may be estimated based on the movement of the link member.

In detail, a location of the emitting member may be estimated based on a current location of a link member. Conversely, to enable the emitting member to face a central point or a target, an operation of a link member may be controlled based on a current location of the emitting member.

Furthermore, when a plurality of robot arms is provided, the plurality of robot arms may be controlled to operate collaboratively through a Jacobian matrix.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A robot comprising:
a central member; and
a plurality of robot arms, each robot arm having one end connected to the central member to rotate on a longitudinal axis of the central member,
wherein the plurality of robot arms are connected to different portions of the central member to rotate independently and incoherently with respect to each other;
wherein the plurality of robot arms comprise:
a plurality of link members;
a plurality of drive members to rotate the plurality of link members;
wherein the plurality of link members are disposed on respective concentric spheres having an identical central point; and
wherein the plurality of link members are provided in a form of arcs and disposed to be spaced from each other radially from the identical central point.

2. The robot of claim 1, wherein the plurality of link members are disposed away from a location at which the plurality of link members are radially spaced from each other to incoherently rotate with respect to each other.

3. The robot of claim 1, wherein extension lines of axes of the plurality of drive members are positioned at an identical point.

4. The robot of claim 3, wherein the plurality of drive members are disposed at end portions of the plurality of link members.

5. The robot of claim 3, wherein the axes of the plurality of drive members are formed to be perpendicular to tangential directions of end portions of the plurality of link members.

6. The robot of claim 3, wherein lengths of the plurality of link members are determined based on angles between axes of the plurality of drive members.

7. The robot of claim 1, further comprising:
a plurality of emitting members provided at other ends of the plurality of robot arms to be moved spherically along trajectories of rotation of the plurality of robot arms, respectively.

8. The robot of claim 7, wherein the plurality of emitting members are disposed to be perpendicular to tangential directions of end portions of the plurality of robot arms, respectively.

9. The robot of claim 7, further comprising:
a plurality of angle adjustment elements disposed at end portions of the plurality of robot arms or the plurality of emitting members to adjust angles at which the plurality of emitting members face a target, respectively.

10. A robot comprising:
a central member;
a first link member to rotate on a longitudinal axis of the central member;
a first drive member disposed at one end of the first link member to transmit a torque to the first link member;
a second link member connected to another end of the first link member to rotate on a first axis;
a second drive member disposed between the first link member and the second link member to transmit a torque to the second link;
a third link member connected to a portion of the central member, the portion differing from a portion to which the first link member is connected, to rotate on the longitudinal axis of the central member;
a third drive member disposed at one end of the third link member to transmit a torque to the third link member;
a fourth link member connected to another end of the third link member to rotate on a second axis;
a fourth drive member disposed between the third link member and the fourth link member to transmit a torque to the fourth link member; and
a plurality of emitting members disposed at end portions of the second link member and the fourth link member to face a target.

11. The robot of claim 10, wherein the longitudinal axis of the central member, the first axis, and the second axis are positioned at an identical location of a target.

12. The robot of claim 10, wherein the first link member and the second link member are disposed farther away from a target than the third link member and the fourth link member.

13. The robot of claim 12, wherein the fourth link member is disposed closer to the target than the third link member.

* * * * *